United States Patent [19]

Natarajan et al.

[11] Patent Number: 6,046,224
[45] Date of Patent: Apr. 4, 2000

[54] 12 (S)—HETE RECEPTOR BLOCKERS

[75] Inventors: Rama Natarajan, Hacienta Heights; Jerry L. Nadler, La Crescenta, both of Calif.

[73] Assignee: City of Hope, Duarte, Calif.

[21] Appl. No.: 09/172,138

[22] Filed: Oct. 14, 1998

Related U.S. Application Data

[60] Provisional application No. 60/062,335, Oct. 15, 1997.

[51] Int. Cl.⁷ .................................................. A61K 31/41
[52] U.S. Cl. ........................ 514/381; 514/560; 514/732; 424/254.1
[58] Field of Search ........................ 424/254.1; 514/381, 514/732, 560

[56] References Cited

U.S. PATENT DOCUMENTS

| | | | |
|---|---|---|---|
| 5,586,496 | 12/1996 | Anderskewitz et al. | 514/637 |
| 5,731,332 | 3/1998 | Anderskewitz et al. | 514/354 |
| 5,795,914 | 8/1998 | Konno et al. | 514/562 |

FOREIGN PATENT DOCUMENTS 9634943   11/1996   WIPO .

OTHER PUBLICATIONS

Arenberger, P., et al., "The Lipoxygenase Inhibitor 2–phenylmethyl–1–naphthol (DuP 654) is a 12(S)–Hydroxyeicosatetraenoic Acid Receptor Antagonist in the Human Epidermal Cell Line SCL–II" *Skin Pharmacol.* 6:148–151 (1993).

Bleich et al. "The Stress–activated C–jun Protein Kinase (JNK) Is Stimulated by Lipoxygenase Pathway Product 12–HETE in RIN m5F Cells" *Biochem. Biophys. Res. Commun.* 230:448–451 (1997).

Wen et al. "Mechanisms of ANG II–Induced Mitogenic Responses: Role of 12–lipoxygenase and Biphasic MAP Kinase" *Am. J. Physiol.* 271 (Cell Physiol. 40): C1212–C1220 (1996).

Natarajan, R. et al., "Mechanism of Angiotensin–II–Induced Proliferation in Bovine Adrenocortical Cells" *Endocrinology,* 131(3):1174–1180 (Sep. 1992).

PCT International Search Report in the corresponding international application.

*Primary Examiner*—James H. Reamer
*Attorney, Agent, or Firm*—Rothwell, Figg, Ernst & Kurz

[57] ABSTRACT

The 12-lipoxygenase product, 12(S)-HETE, mediates hyperproliferative and hyperplastic responses seen in atherosclerosis, diabetes, Parkinson's disease, Alzheimer's, stroke-induced nerve damage and cancer. 12-HETE also mediates inflammation and cell death in some cell systems, particularly B-islet cells of the pancreas. The present invention involves amelioration of disease states mediated by 12(S)-HETE by blocking specific 12(S)-HETE receptors.

15 Claims, 9 Drawing Sheets

12 (S)— HETE RECEPTOR BLOCKERS

This application claims priority from provisional application Ser. No. 60/062,335, filed Oct. 15, 1997.

STATEMENT REGARDING FEDERALLY SUPPORTED RESEARCH

This invention was made with government support under Grant No. DK 39721 awarded by the National Institutes of Health (NIDDK). The government may have certain rights in the invention.

BACKGROUND OF THE INVENTION

1. Field of the Invention

The present invention relates to blockade of the 12(S)-HETE cell surface receptor as a treatment for conditions of the body which result from stimulation or overstimulation of the receptor. 12(S)-HETE, a product of the 12-lipoxygenase pathway, mediates the hyperproliferative and inflammatory responses present in such diseases as atherosclerosis, psoriasis, diabetes, and cancer. 12(S)-HETE also mediates inflammatory responses and cell death in some cell types, particularly pancreatic islet beta cells and nerve cells. Blockade of the 12(S)-HETE receptor ameliorates the symptoms and arrests the mitogenic cellular responses.

2. Background

Lipoxygenases (LO) are metabolic enzymes which catalyze the stereospecific oxygenation of polyunsaturated fatty acids to hydroperoxy fatty acids (Hamberg et al., *J. Biol. Chem.* 242:5329–5335 (1967)). The physiological function of 12-LO, the mammalian enzyme which catalyzes the oxygenation of arachidonic acid to (S)-12-hydroperoxyeicosatetraenoic acid (12-HPETE) and (S)-12-hydroxyeicosatetraenoic acid (12(S)-HETE), is unclear. 12-LO exists as two isoforms which are the products of different genes, leukocyte-type 12-LO and platelet-type 12-LO, which share 65% homology at the amino acid level (Izumi et al., *Proc. Natl. Acad. Sci., USA* 87:7477–7481 (1990); Funk et al., *Proc. Natl. Acad. Sci. USA* 87:5638–5642 (1990)). The products of the 12-LO pathway, such as 12(S)-HETE, have been shown to play important roles in diseases such as atherosclerosis, diabetes, and cancer. 12(S)-HETE has direct mitogenic and hypertrophic effects in vascular cells. It is also a potent chemoattractant for vascular smooth muscle cells (VSMC) and can activate oncogenes such as c-fos and ras and key growth-related kinases such as mitogen-activated protein kinases (ERK, JNK, PAK, p38) and protein kinase C. New results also indicate that 12(S)-HETE can directly increase monocyte binding. Human aortic endothelial cells incubated with 12(S)-HETE for four hours prior to monocyte adhesion assays resulted in an average increase of 3-fold (range of 1.5–5 fold) in monocyte binding as compared to untreated cells. In addition, glucose-induced monocyte adhesion was abrogated by the inhibition of 12-LO using both phenidone, a non-specific LO inhibitor, and baicalein, a more specific 12-LO inhibitor. The adhesion caused by 12-LO products appears to be monocyte-specific.

The 12-LO pathway is activated in pancreatic islets by cytokines and may participate in islet cell destruction. In inflammatory diseases, this pathway plays crucial roles in transmitting distinctive signals within the cell. Using inhibitors of the 12-LO enzyme pathway, researchers have been able to prevent inflammation and cellular damage. Furthermore, VSMC cultured under high glucose (HG) conditions produce increased amounts of 12(S)-HETE (Natarajan et al., *Proc. Natl. Acad. Sci. USA* 90:4947–4951 (1993). Thus, this pathway may be key to the accelerated cardiovascular disease observed in diabetes.

The LO pathway also plays a role in the growth-promoting effects of angiotensin II (AII) and in the chemotactic effects of platelet-derived growth factor: the products of the 12-LO pathway, and 12(S)-HETE in particular, are associated with the hypertrophic, hyperplastic, and mitogenic effects induced by AII. Wen et al., 271 *Am. J. Physiol.* (40 Cell Physiol.) C1212–C1220 (1996); (Natarajan et al., *Hypertension* 23:I142–I147 (1994)). The proliferative effects of AII are inhibited by baicalein, a LO inhibitor. The mitogenic effects of 12(S)-HETE are similar to those of AII and are abrogated by pertussis toxin, implicating a G-protein mechanism. The 12-LO enzyme pathway is known to generate proinflammatory mediators in a variety of cells (O. R. Etingin et al., *J. Lipid Res.* 31:299–305 (1990); V. A. Folcik and M. K. Cathcart *J. Lipid Res.* 34:69–79 (1993)). Human and rat pancreatic B-cells specifically express active leukocyte type 12-LO (V. P. Shannon et al., *Am. J. Physiol.* 263:E828–E836 (1992): D. S. Bleich et al., *Endocrinol.* 136:5736–5744 (1995)). Recent evidence implicates products of the 12-LO pathway in nerve cell death associated with Parkinson's disease, Alzheimer's disease and other inflammatory nerve cell conditions (*Neuron* 19:453–463 (1997)).

Because 12(S)-HETE has several biological effects linked to cellular growth in vascular smooth muscle and cardiac fibroblasts (Natarajan et al., *Hypertension* 23:I142–I147 (1994); Wen et al., *Am. J. Physiol.* 211:C1212–C1220 (1996)), it is implicated in the etiology of cardiovascular disease. Further evidence that 12(S)-HETE is responsible for the cellular responses seen in cardiovascular disease in diabetic patients includes the fact that monocyte binding to cultured human aortic endothelial cells increases in chronic high glucose conditions, and that this is coincident with increased formation of LO products such as 12(S)-HETE. (Kim et al., *Diabetes* 43:1103–1107 (1994)). Furthermore, treatment of aortic endothelial cells with 12(S)-HETE increases monocyte binding, likely by stimulating JNK activity and inducing CS-1. 12(S)-HETE can also stimulate vascular endothelial growth factor (VEGF) gene expression in vascular smooth muscle (*Am. J. Physiol.* 273: H2224–H2231 (1997)). VEGF has been linked to angiogenesis in diabetic retinopathy, tumor growth and atherosclerotic vascular disease. 12(S)-HETE is also regarded as a mediator of inflammation and hyperproliferation of the skin (Arenberger et al., *Skin Pharmacol.* 6:148–151 (1993); Gross et al., *J. Invest. Dermatol.* 94:446–451 (1990)) and is therefore implicated in skin diseases. 12(S)-HETE has been shown to enhance tumor cell adhesion to endothelial cells. (Honn et al., *Cancer Metastasis Rev.* 13:365–396 (1994)). 12(S)-HETE can directly increase p21 activated kinase (PAK). The effect appears to be through activation of small GTP binding proteins such as RAC and through activation of PI3K.

The precise mechanisms of 12(S)-HETE action are not clear, however recent studies have shown that the LO product, 12(S)-HETE, activates c-jun amino terminal kinase (JNK) (Wen et al., *Circ. Res.* 81:651–655 (1997)). JNK is a small GTP-binding protein and a member of the MAP kinase family which is involved in cellular growth, inflammation, and apoptosis (Force et al., *Circ. Res.* 78:947–953 (1994)) and in cell cycle progression through $G_1$ (Olson et al., *Science* 269:1270–1272 (1995)). Evidence shows that JNK can serve as a positive or negative modulator of cell growth in different cells. Olson et al., 269 *Science* 1270–1272

(1995); Yan et al., 372 *Nature* 798–800 (1994). 12(S)-HETE activation of JNK may also be the mediator of cytokine-induced pancreatic B-cell damage (Bleich et al., *Biochem. Biophys. Res. Commun.* 230:448–451 (1997)).

Newer evidence indicates that the growth factor and potent vasoconstrictor AII, linked to type-1 receptor activation, can activate JNK and PAK (Wen et al., *Circ. Res.* 81:651–655 (1997); Schmitz et al., *Circ. Res.* 82:1272–1278 (1998)). Furthermore, AII can modulate serum deprivation-induced apoptosis by increasing JNK activity in vascular smooth muscle cells, Sueror et al., *Circulation, Supp.* 1, I-281 (1994), mediated by lipids derived from the 12-LO pathway, such as 12(S)-HETE. This indicates that 12-LO products participate in JNK activation at least in part through $G_1$-protein signaling. The ability of pertussis toxin to block the activation of JNK by 12(S)-HETE also supports the theory that 12(S)-HETE is a mediator of AII-induced JNK activation through a $G_1$-mediated pathway.

While several studies have demonstrated the potent biological effects of lipoxygenase products, the mechanisms of action of these effects are not known. Some reports have hinted at the presence of 12(S)-HETE receptors on transformed cells. Binding sites for 12(S)-HETE have been detected in carcinoma cells (Herbertsson and Hammarstrom, FEBS 298:249–252 (1992), on melanoma cells (Liu et al., *Proc. Natl. Acad. Sci. USA* 92:9323–9327 (1995), and in a human epidermal cell line (Gross et al., *J. Invest. Dermatol.* 94:446–451 (1990); Suss et al., *Exptl. Cell Res.* 191(2):204–208 (1990)).

The 12(S)-HETE receptors described in carcinoma cells are cytosolic receptors (Herbertsson and Hammarstrom, *Biochem. Biophys. Acta* 1244:191–197 (1995)), activation of which may mediate 12(S)-HETE induced mRNA production of genes coding for the integrin $\alpha_{IIb}\beta_3$ (Chang et al., *Biochem. Biophys. Res. Comm.* 176:108–113 (1991)). The localization of this receptor is different from plasma cell membrane receptors coupled to a G-protein and acting through second messengers. 12(S)-HETE receptors on the cell surface of murine melanoma cells have been described. These receptors stimulate the second messengers diacylglycerol and inositol phosphate$_3$ via a G-protein mechanism, resulting in protein kinase $C_2$ activation. (Liu et al., *Proc. Natl. Acad. Sci. USA* 92:9323–9327 (1995)). The binding of 12(S)-HETE to these receptors was blocked by 13(s)-hydroxyoctadecadienoic acid, a LO metabolite of linoleic acid, ablating the 12(S)-HETE increased adhesion of the cells to fibronectin. These authors suggest 12(S)-HETE may act in a "cytokine" fashion to regulate responses of adjacent tumor cells, endothelial cells, and platelets.

Receptors for 15-HETE have been identified in mast/basophil (PT-18) cells and were shown to possess properties of G-protein-coupled receptors (Vonakis and Vanderhoek, *J. Biol. Chem.* 267:23625–23631 (1992). Specific binding of 15-HETE to these receptors stimulated 5-LO, and while 12(S)-HETE was found to be an effective competitor of [$^3$H]15-HETE binding to PT-18 cells, suggesting that 12(S)-HETE binds to the specific 15-HETE receptor, the binding of 12(S)-HETE did not stimulate the lipoxygenase. Very recent studies have indicated the activation of a cell surface G-protein-coupled 5-HETE receptor in neutrophils (Capadici et al., *J. Clin. Invest.* 102:165–175 (1998)).

The high affinity 12(S)-HETE-specific receptors in a human epidermal carcinoma cell line were induced by γ-IFN (Gross et al., *J. Invest. Dermatol.* 94:446–451 (1990)). Saturation binding of 12(S)-HETE to these receptors did not stimulate cell growth, therefore, the function of these receptors in the skin is entirely speculative, and not related to the AII-induced cellular effects mediated by cell surface 12(S)-HETE receptors in fibroblasts overexpressing the AII receptor and potentially in vascular smooth muscle cells. Two recent studies have indicated two additional agents which could reduce 12(S)-HETE binding (Kemeny and Ruzicka, *Agents Actions* 32:339–342 (1991); Kemeny et al., *Arch. Dermatol. Res.* 283:333–336 (1991)).

Specific inhibitors of 12-LO have been described. Gorins et al., *J. Med. Chem.* 39:4871–4878 (1996). In that study, a series of substituted (carboxyalkyl)benzyl ethers were found to be selective inhibitors of leukocyte-type 12-LO. These inhibitors of 12-LO acted by serving as structural analogs for the enzyme. Gorins et al., *J. Med. Chem.* 39:4871–4878 (1996). The 5-LO inhibitor, 2-phenylmethyl-1-naphthol (DuP654), has also been shown to specifically inhibit binding of 12(S)-HETE to receptors on the human epidermal cell line SCL-II. Arenberger et al., *Skin Pharmacol* 6:148–151 1993).

In vivo, inhibition of 12-LO has lowered blood pressure in several models of hypertensive animals, including rats (Stern et al., *Am. J. Physiol.* 257:H434–H443 (1989); Nozawa et al., *Am. J. Physiol.* 259:H1447–H1780 (1990)). In addition, blockage of 12-LO activity has alleviated the growth-factor induced effects of 12-HETE in vascular cells. This, along with the known increased expression of 12-LO observed in animal models of diabetes (Gu et al., *Am. Diabet. Assoc. Meeting* (1996); Natarajan et al., *Intl. Aldosterone Meeting* (1998)) and diabetes induced accelerated atherosclerosis (Gerrity et al., *Circulation* I175 (1997)) strongly implicate 12-HETE and the 12-LO pathway in the etiology of these diseases. The harmful effects of 12-LO activation are ameliorated by blocking the production of 12(S)-HETE, providing the rationale for a method of treatment which focusses on preventing 12(S)-HETE binding to its receptor.

There is currently no inhibitor of 12(S)-HETE receptor binding in clinical use. Due to the existence of several isoforms of 12-LO, blockage of the 12-HETE receptor is a more specific and direct way to correct a disease state in which there is increased production of 12(S)-HETE or the receptors are up-regulated. This invention therefore, could provide the basis for the development of interventions to reduce cardiovascular disease, diabetes, and cancer.

SUMMARY OF THE INVENTION

The present invention relates to a method of inhibiting the effects of the LO product 12(S)-HETE by blocking 12(S)-HETE receptors comprising the administration of an effective amount of a 12(S)-HETE receptor antagonist or an antibody directed against a cell surface 12(S)-HETE receptor. The blockade of 12(S)-HETE receptors provides a means for ameliorating the proliferative and mitogenic effects of glucose, PDGF or AII-induced 12(S)-HETE production, or direct effects of 12(S)-HETE inflammatory actions.

DETAILED DESCRIPTION OF THE INVENTION

Figure 1:
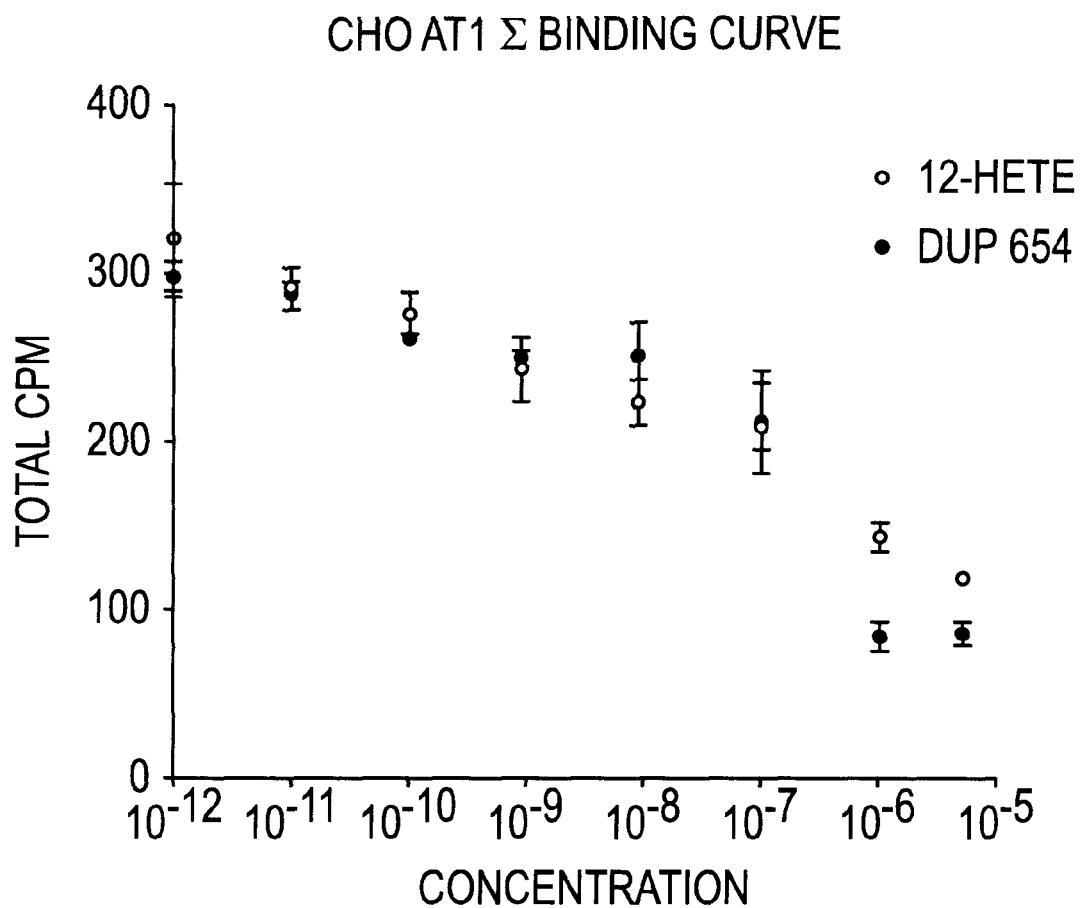
FIG. 1 depicts the binding of tritiated 12(S)-HETE and DuP654 to CHO-AT$_{1a}$ cells at increasing concentrations of unlabeled 12(S).HETE.

Angiotensin II (AII) has been shown to stimulate, through the AII AT, receptor, 12-LO activity in murine macrophages, Scheidegger et al., *J. Biol. Chem.* 272:21609–21615 (1997), and in smooth muscle cells, Natarajan et al., *Proc. Natl. Acad. Sci., USA* 90:4947–4951 (1993); Kim et al., *Atheroscler. Thromb. Vasc. Biol.* 15:942–948 (1995). Stimulation of the 12-LO pathway in murine macrophages resulted in an increase of monocyte chemotaxis (Scheidegger et al., (in press, 1997)), presumably through modification of LDL. This activity links AII activation of 12-LO to atherosclerotic disease.

The potential mechanisms of AII-induced mitogenic effects in a Chinese hamster ovary fibroblast cell line overexpressing the rat vascular type 1a AII (AT$_{1a}$) receptor have recently been examined. See Wen et al *Am. J. Physiol.* 270 (Cell Physiol. 40): C1212–C1220 (1996). AII had mitogenic effects in these cells, leading to a sustained increase in DNA synthesis as well as cell number. It was also observed in these cells that the 12-lipoxygenase product, 12(S)-HETE, also had direct mitogenic effects in these cells. See Wen et al., *Am. J. Physiol.* 270 (Cell Physiol. 40): C1212–C1220 (1996). Furthermore, 12(S)-HETE did not have any mitogenic effects in mock transfected cells. The addition of 12(S)-HETE to these CHO-AT$_{1a}$ cells led to a significant increase in the activity of the key growth-related kinases, mitogen activated protein kinase (Wen et al., *Am. J. Physiol.* 270 (Cell Physiol. 40): C1212–C1220 (1996)), and c-jun amino terminal kinase (Wen et al., *Circ. Res.* 81:651–655 (1997)). This work has suggested that over expression of the AT$_{1a}$ receptor plays a role in inducing a putative 12(S)-HETE receptor, which is supported by the observation that the mitogenic effects of 12(S)-HETE were completely abrogated by pretreatment of the cells with pertussis toxin. Thus, the effects of 12(S)-HETE may be mediated by a Gi protein-coupled receptor. See example 3, below. Application of AII to CHO-AT$_{1a}$ cells resulted in a 2-fold increase in 12(S)-HETE formation and cell proliferation. These proliferative effects were inhibited by the 12-LO inhibitor, baicalein.

In accordance with the present invention, a 12-HETE receptor has been discovered and characterized. For the first time, a specific high affinity 12(S)-HETE receptor has been identified. Chinese hamster ovary (CHO) fibroblasts that stably overexpress the rat vascular angiotensin type 1a receptor (CHO-AT$_{1a}$) have been found to carry this receptor. This receptor is not present in mock transfected cells. Experiments have been performed which indicate that this receptor has characteristics of a G-protein coupled receptor. Furthermore, there is evidence of crosstalk between this receptor and the AT$_{1b}$ receptor, since a specific antagonist, Losartan, was able to partially block the binding of 12(S)-HETE to the cells and also blocked the mitogenic effects of 12(S)-HETE. Furthermore, a 12(S)-HETE receptor antagonist blocked 12(S)-HETE mitogenic effects and partially blocked AII mitogenic effects. Increased actions of vasoactive and growth promoting agents, such as angiotensin II, under pathologic conditions may up-regulate 12(S)-HETE receptors. Hence, further studies of this receptor in vascular and other cells, as well as the development of specific receptor antagonists, are expected to be therapeutically important.

It has also been found that hyperglycemic conditions result in both increased monocyte binding to human aortic endothelial cells (HAEC) and increased 12(S)-HETE and 15-HETE activity. Neutrophil binding is not increased. In HAEC incubated in vitro with 12-LO products, increased monocyte binding, JNK activation, and induction of CS-1 fibronectin were detected, suggesting that the upregulation of 12-LO activity seen in hyperglycemia may exacerbate atherosclerosis by stimulating adhesion of monocytes through JNK activation and CS-1 production. For example, monocytes inabated with $10^{-7}$ M 12(S)-HETE for 12 minutes at room temperature or at 37° C. prior to monocyte adhesion assay demonstrated increased adhesion over untreated cells. See Example 10.

Blockade of 12(S)-HETE receptor binding therefore is a new method of treating disorders associated with increased 12-lipoxygenase expression and activity. These diseases include atherosclerotic cardiovascular disease, glucose and diabetes-induced complications, cytokine-induced inflammatory cellular effects, and tumor cell growth and metastasis.

The kinetics of radioactive [$^3$H]12(S)-HETE binding to these cells at 4° C. have been examined. These studies have revealed the presence of specific high affinity binding sites for 12(S)-HETE on these cells. Specificity was determined by the observation that this binding of tritiated 12(S)-HETE was displaced by unlabeled 12(S)-HETE. A one site fit model yielded a Kd of 38.4 nM. See Example 1. The binding kinetics of [$^3$H]12(S)-HETE have revealed the presence of specific high affinity 12(S)-HETE binding sites on CHO-AT$_1$ cells, but not in mock transfected cells; these results suggest that AII-induced mitogenic effects involve the production of reactive oxygen species and LO products via activation of G-protein-coupled receptors.

Figure 3:
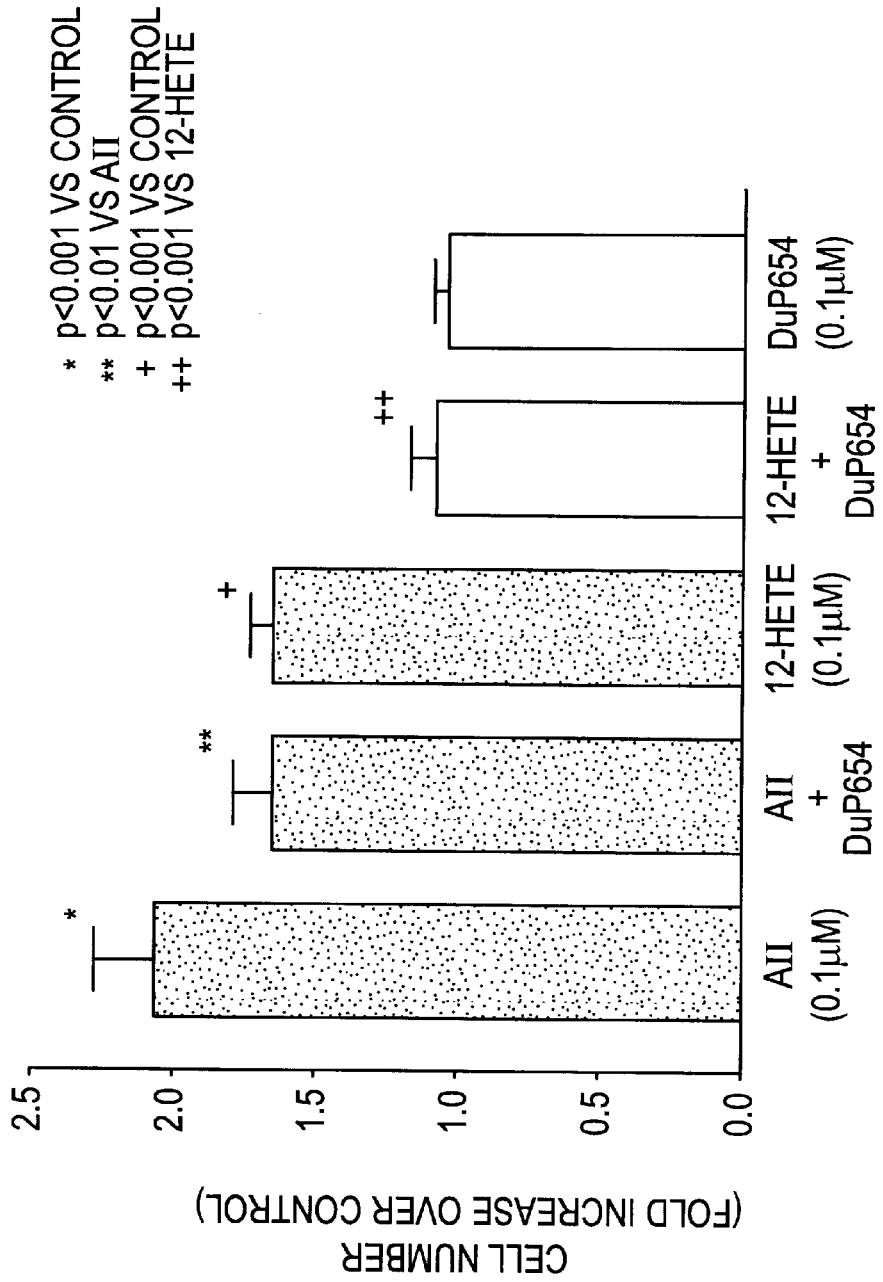
FIG. 3 shows the effect of the 12(S)-HETE receptor antagonist, DuP654, on AII- and 12(S)-HETE-induced growth in CHO-AT$_{1a}$ cells.
Figure 4:
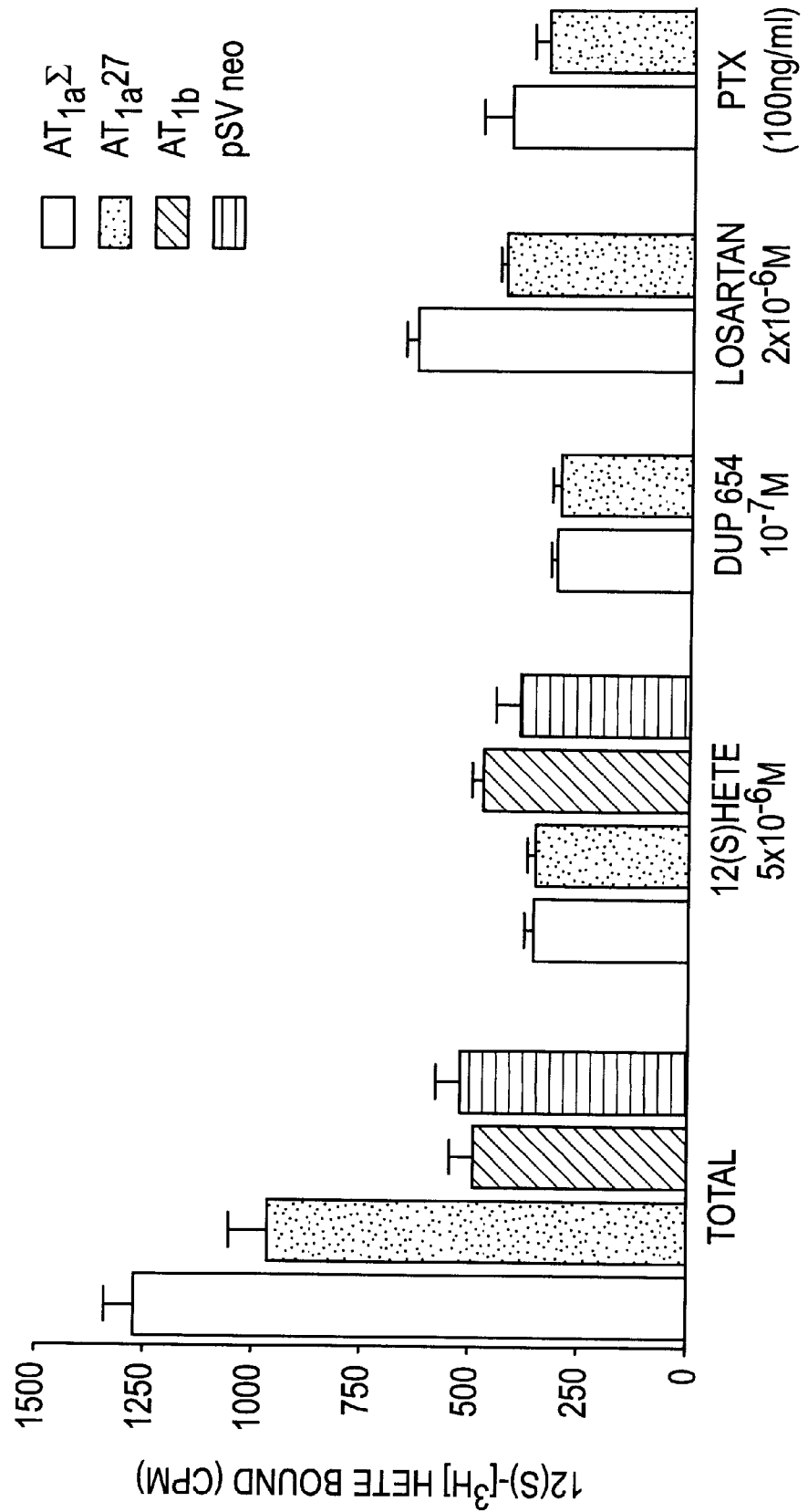
FIG. 4 shows the effect of three agents which bind to CHO-AT$_{1a}$ cells, DuP654(a 12(s)HETE receptor antagonist), Losartan (a specific AII$_{1a}$ receptor antagonist) and pertussis toxin, relative to 12(S)-HETE effects. Inhibition of labeled 12(S)-HETE binding sites on AT$_{1a}$Σ and At$_{1a}$27 (2 cloned overexpressing AT$_{1a}$) cells are shown and pSV neo mock transfected cells.
Figure 5:
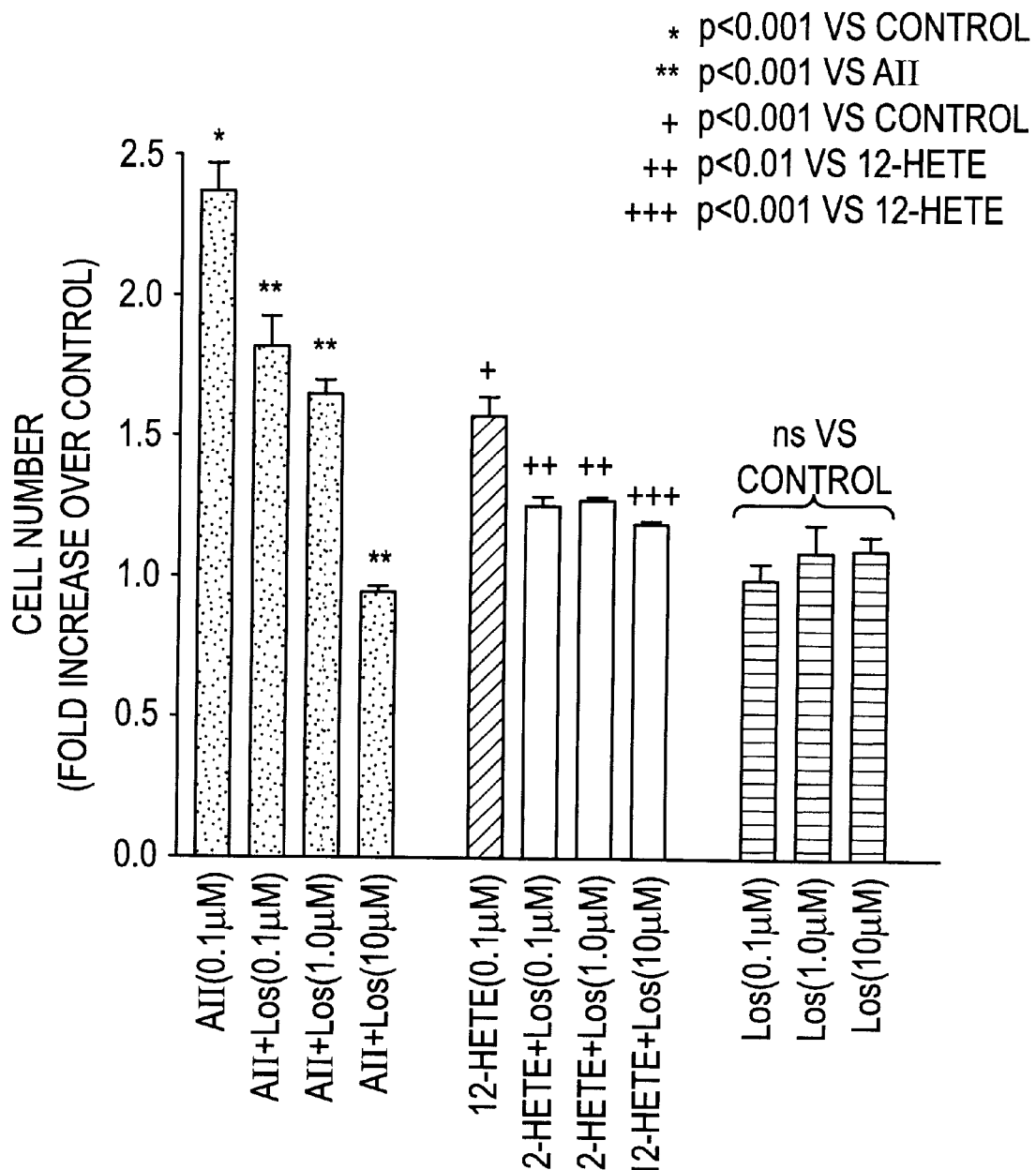
FIG. 5 shows the effect of Losartan on AII and 12(S)-HETE-induced mitogenesis in CHO-AT$_{1a}$ cells.
Figure 6A:
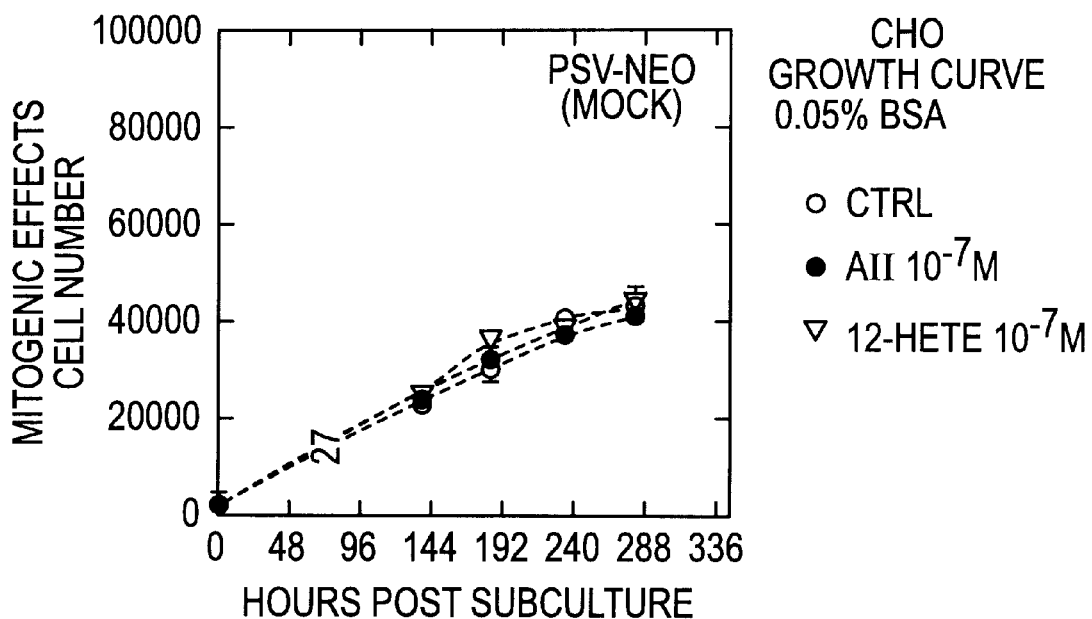
FIG. 6 shows the mitogenic effects of AII and 12(S)-HETE on Psv neo mock transfected cells, AT$_{1a}$ expressing cells and AT$_{1b}$ expressing cells.
Figure 6B:
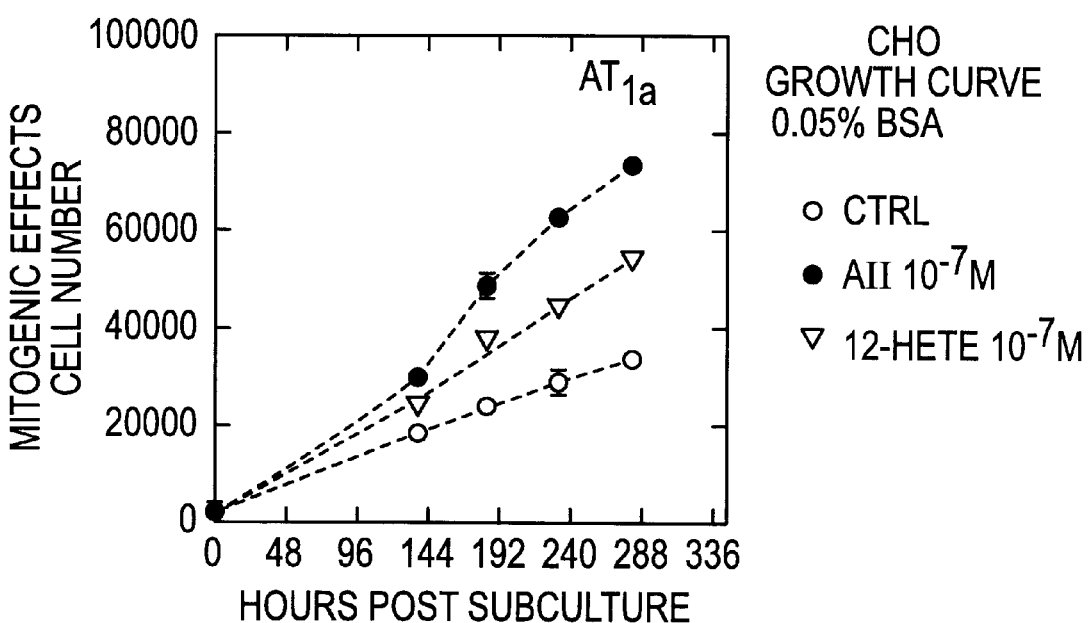
Figure 6C:
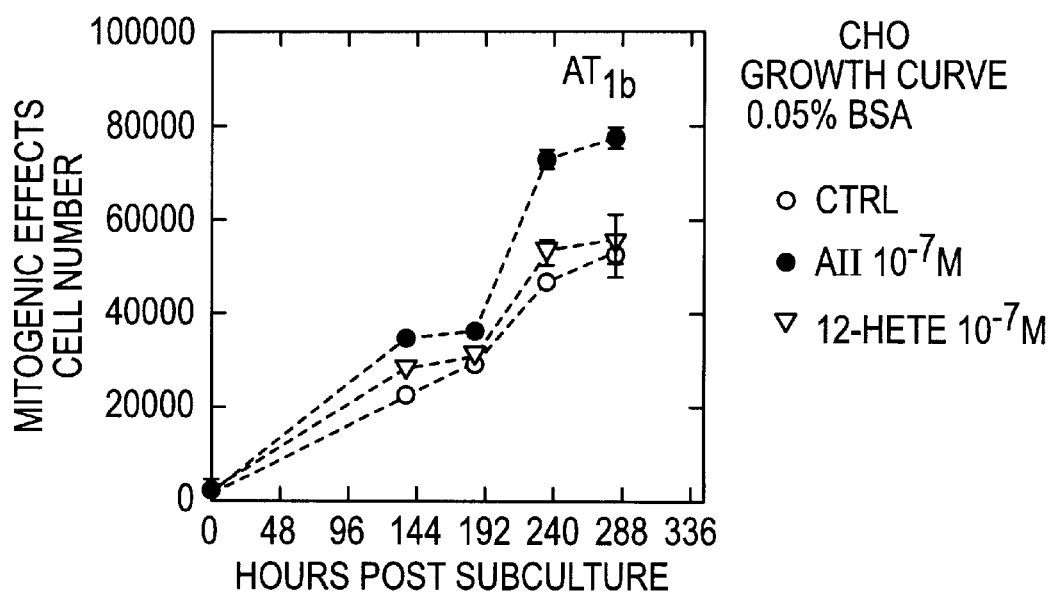
Figure 7:
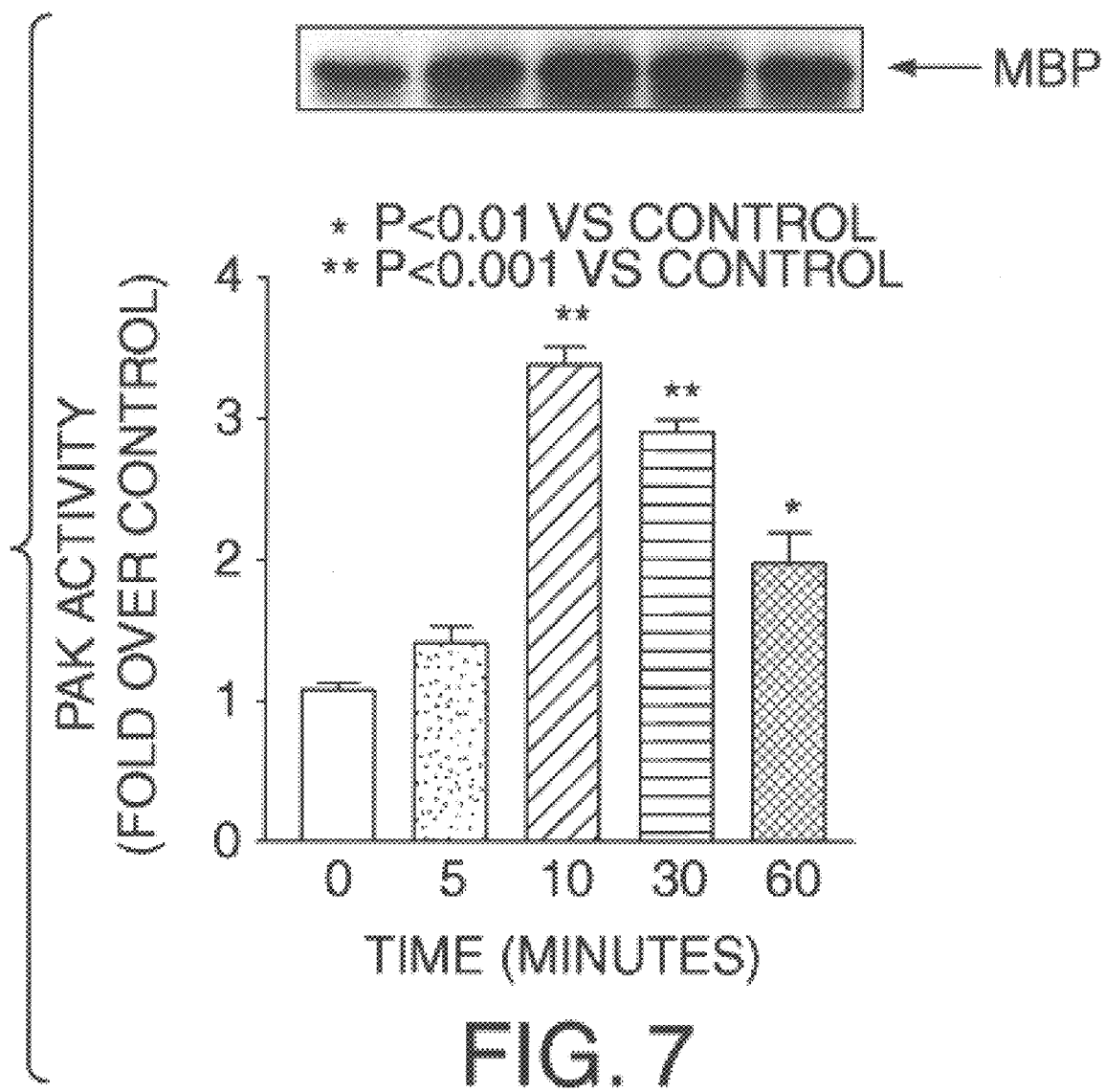
FIG. 7 shows the time course of PAK activation by 12(S)-HETE ($10^{-7}$ M) in CHO-AT$_{1a}$ cells.

DuP654 could completely inhibit 12(S)-HETE-induced mitogenic effects. DuP654 significantly reduced cell growth induced by either AII or 12(S)-HETE at a concentration of 0.1 μM. Tritiated 12(S)-HETE binding was also blocked by pertussis toxin (FIG. 3). Pertussis toxin has been shown to ablate 12(S)-HETE-induced mitogenic effects (Wen et al., *Am. J. Physiol.* 270 (*Cell Physiol.* 40): C1212–C1220 (1996)), implicating the involvement of a G$_1$ protein-coupled receptor. Losartan, a specific angiotensin AT$_{1a}$ receptor antagonist now in clinical use for the treatment of hypertension, partially blocked tritiated 12(S)-HETE binding (FIG. 4). Similarly, it partially blocked 12(S)-HETE-induced mitogenic effects in these CHO-AT$_{1a}$ cells, while fully inhibiting AII-induced proliferative effects (FIG. 5). 12(S)-HETE had mitogenic effects only in CHO-AT$_{1a}$ cells, but not in mock transfected cells (pSVneo), nor in CHO cells overexpressing the angiotensin AT1b receptor (FIG. 6).

This invention involves a method for inhibiting the effects of 12(S)-HETE by administration of an effective amount of a 12(S)-HETE receptor antagonist. The method is useful for the treatment or prophylaxis of conditions in which 12(S)-HETE receptor activation contributes to adverse effects. For example, the method of this invention may be employed for the treatment or prophylaxis of atherosclerotic cardiovascular disease, glucose-induced complications of diabetes, cytokine-induced inflammatory diseases and tumor cell growth and metastasis.

The 12(S)-HETE receptor antagonist may be any agent that blocks or significantly inhibits binding of 12(S)-HETE to its receptor. Such agents include DuP654 (2-phenylmethyl-1-napthol), Losartan (2-N-butyl-4-chloro-5-hydroxymethyl-1-[(2'-(1H-tetrazol-5-yl)biphenyl-4-yl) methyl]imidazole, potassium salt), pertussis toxin, 12(S)-HETE analogs, peptides and peptide analogs having affinity for the binding site on the 12(S)-HETE receptor (especially antibodies which can block 12(S)-HETE receptors), antibodies to the 12(S)-HETE receptor, and the like.

The determination of appropriate, well-tolerated dosage forms for administration to humans for use in the present invention is within the ordinary skill in the art. Such dosage forms include tablets, capsules, syrups, suspensions, drops, injectable solutions, lozenges, implants, transdermal patches, and other dosage forms well known in the art for enteral or parenteral administration. Based on in vitro experiments on the effect of 12(S)-HETE blocking drugs on 12(S)-HETE binding, a dose of between about 0.5 and about 30 mg/kg/day would be effective in blocking 12(S)-HETE receptors in humans in vivo, and preferably from about 1 to about 10 mg/kg/day.

The present invention is further illustrated by the following examples, which are not intended to be limiting.

EXAMPLES

Example 1

Figure 2:
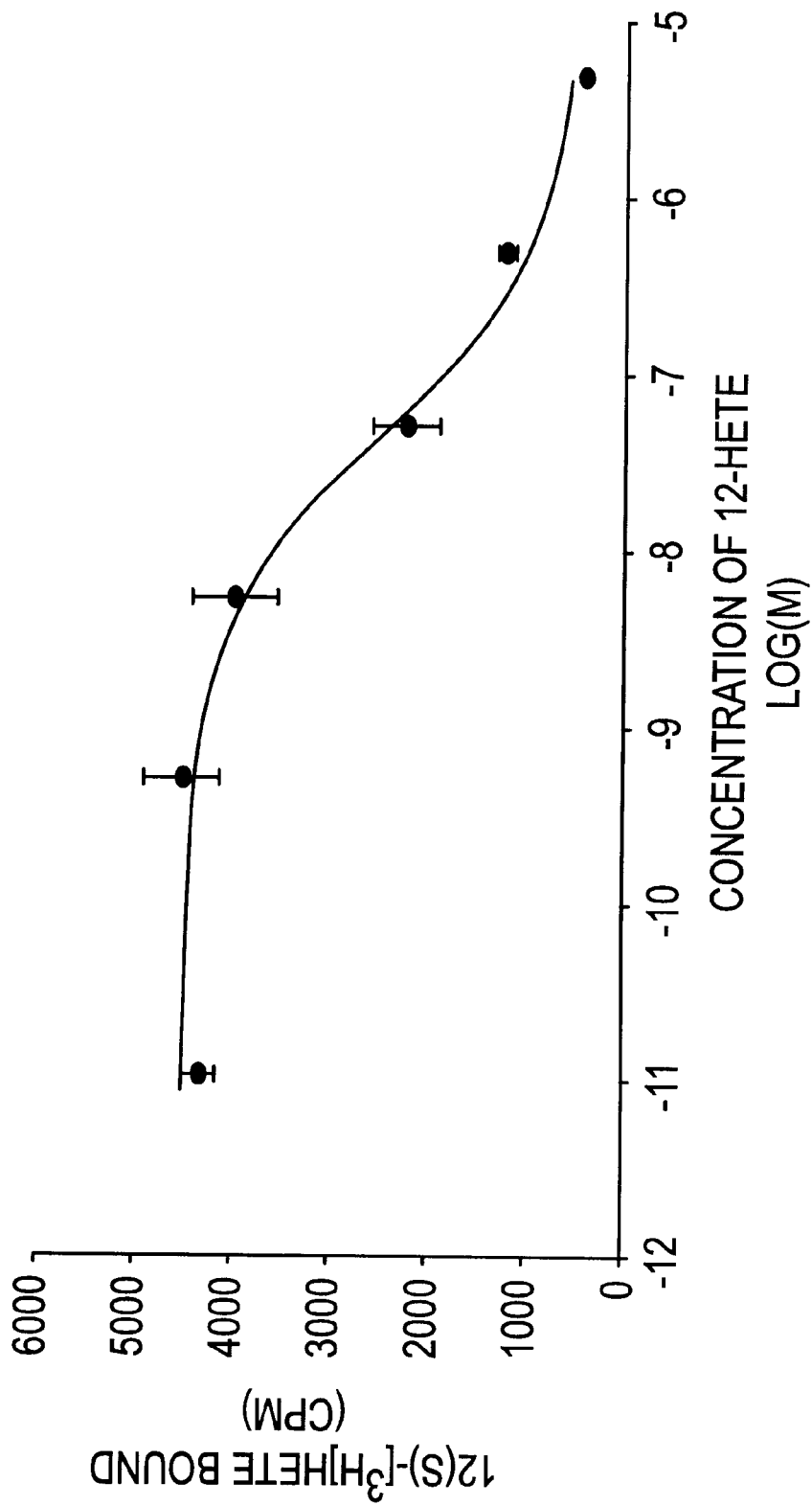
FIG. 2 shows a competitive binding curve of tritiated and unlabeled 12(S)-HETE with CHO-AT$_{1a}$ cells.

Kinetics of [$^3$H]12(S)-HETE binding to CHO-AT$_{1a}$ cells. FIGS. 1 and 2 are a competition curves which examine the specificity of [$^3$H]12(S)-HETE binding. CHO-AT$_{1a}$ cells were grown to confluence in 24 well tissue culture dishes in HAM's F12 medium containing 10% fetal calf serum. The cells were then rinsed and placed in fresh medium, HAM's F12/HEPES with no other additives (450 u1 per well). Serial dilutions of unlabeled 12(S)-HETE or DuP654 were added to the wells. Commercial unlabeled 12(S)-HETE (BioMol Corp.) was dried and reconstituted in ethanol to obtain a stock solution of 5 mM. DuP654 was dissolved in DMSO to get a stock solution of 5 mM. These were then serially diluted and added in a volume of 1 u1 to the wells to obtain the final concentrations indicated. Then [$^3$H]12(S)-HETE (10,000 cpm in a volume of 50 u1 per well) was added from a stock solution obtained by adding the tracer to the medium. The plates were then incubated at 4° C. with continuous shaking for 2 hr. The cells were then washed 2 times with cold PBS and lysed in 0.3N NaOH (200 u1). Radioactivity in the cell lysates was quantitated in scintillation counter. Affinities and binding constants were obtained using Matlab computer software (Mlab, Civilized Software Inc., Bethesda, Md.).

This experiment revealed the presence of specific high affinity binding sites for 12(S)-HETE on these cells. A one site fit model yielded a Kd of 38.4 nM. Specificity was determined by the observation that this binding of [$^3$H]12(S)-HETE was displaced by unlabeled 12(S)-HETE.

Example 2

Reduction of cell growth induced by AII or 12(S)-HETE.

DuP654 significantly reduced cell growth induced by either AII or 12(S)-HETE at a concentration of 0.1 μM. Complete inhibition of 12(S)-HETE induced mitogenic effects was seen. See FIG. 3.

Example 3

Blockade of the 12(S)-HETE receptor by a specific antagonist.

Tritrated 12(S)-HETE binding is blocked by unlabeled 12(S)-HETE. See FIG. 4. DuP654, a 12(S)-HETE receptor antagonist, was shown also to block 12(S)-HETE at a concentration of 0.1 μM in both AT$_{1a}$Σ and AT$_{1a}$27 cell types, two clones of CHO cells which overexpress the AII$_{1a}$ receptor. See FIG. 4. The cells were grown as described in Example 1.

Example 4

Blockade of 12(S)-HETE binding by pertussis toxin. Cells were grown as described in Example 1. Prior to addition of drug (12(S)-HETE or DuP654) to the cells, the cultures were preincubated in HAM's F12 medium +0.1% BSA for two hours at 37° C. with or without 100 ng/ml pertussis toxin. Serial dilutions of unlabeled 12(S)-HETE or DuP654 were added, followed by [$^3$H]12(S)-HETE as described for Example 1. After incubation and washing, radioactivity in the cell lysates was quantitated. See FIG. 4. As discussed above, pertussis toxin could also ablate 12(S)-HETE-induced mitogenic effects. This implicates the involvement of a G$_i$-protein-coupled receptor.

Example 5

Partial blockade of 12(S)-HETE mitogensis by the specific angiotensin AT$_{1a}$ receptor antagonist, Losartan, in CHO-AT$_{1a}$ cells. (FIG. 5) CHO-AT$_{1a}$ cells were plated in 12-well dishes (about 5–10,000 cells per well) for 24 hr. in growth medium consisting of HAM's, F12+10% FCS. They were then serum depleted for 72 hours by replacing the medium with HAM's F12+0.1% BSA. This medium was then freshly replaced along with AII or 12-HETE (0.1 μM each) prior to addition of drug to the cells. Losartan was added as a solution in water to the cells 15 min. prior to the addition of AII or 12-HETE. The final concentration of Losartan was as indicated in FIG. 4. Fresh medium containing the same concentrations of AII or 12(S)-HETE plus Losartan was replaced every 48 hours. At the end of 8 days, the medium was removed, and 1 ml trypsin was added per well followed by 1 ml isoton after 3 min. These trypsinized cells were counted on a Coulter counter. Losartan partially blocked 12(S)-HETE-induced mitogenic effects and fully blocked AII-induced proliferative effects. See FIG. 5). Losartan also partially blocked [$^3$H] 12-HETE binding (FIG. 4).

Example 6

Dependency of 12(S)-HETE mitogenic effects on expression of the AT$_1$a receptor.

The three cell lines, CHO-AT$_{1a}$, CHO-AT$_{1b}$ and mock transfected CHO cells were gifts from Dr. Eric Clauser (Inserm Unit, Paris, France). These cells were plated in 12 well dishes in HAM's F12 medium +10% FCS. After 72 hours serum depletion in HAM's F12+0.05% FCS, the cells were treated with AII or 12(S)-HETE (0.1 µM). Cells counts (after trypsinization) were taken at 48 hour intervals and fresh medium along with AII or 12-HETE added at these 48 hour intervals. 12(S)-HETE had mitogenic effects only in CHO-$AT_{1a}$ cells, but not in mock transfected cells (pSVneo), nor in CHO cells overexpressing the angiotensin $AT_{1b}$ receptor. See FIG. 6.

Example 7

PAK activation by 12(S)-HETE.

CHO-$AT_{1a}$ cells were gently washed and placed in depletion medium (HAM's F-12 medium containing 1 mg\ml BSA and 20 mM HEPES, ph 7.4) for 72 hours prior to use. After incubation for 30 minutes, the cells were treated with $10^{-7}$ M 12(S)-HETE or with ethanol. The 12(S)-HETE treatment was terminated by washing twice with PBS and adding 300 µl lysis buffer (50 mM HEPES. pH 7.5, containing 150 mM NaCl, 5 mM $MgCl_2$, 1 mM EGTA, 50 mM NaF, 10 mM sodium pyrophosphate, 1% NP-40, 2.5% glycerol and 1 mM $Na_3VO_4$ containing the protease inhibitors phenylmethylsulfonyl fluoride, leupeptin, and aprotonin) followed by sedimentation at 14,000× g at 4° C. for ten minutes. Protein determination was performed by the Bradford method. The top panel shows a representative autoradiogram of phosphonycated myelin basic protein (MBP) bands from a gel. PAK activity was measured as follows. First, 300 µg of lysate protein was incubated with PAK antibody (1:20) in lysis buffer overnight at 4° C., followed by incubation with 60 µl of a 50% slurry of protein A beads for 60 minutes. After washing three times with lysis buffer and twice with kinase buffer (50 mM HEPES, pH 7.4, 10 mM $MgCl_2$, 10 mM $MnCl_2$, and 0.2 dithiothreitol) containing 2 µl MBP, 20 µM ATP and 5 µCi [$\gamma$-$^{32}$P] ATP, the kinase activity was measured in 60 µl kinase buffer. After incubation for 30 minutes at 30° C., the reaction was stopped with 5× Laemmli sample buffer and resolved on a 12% SDS-polyacrylamide gel, followed by autoradiography. The bottom panel shows the densitometric quantitation of PAK activity stimulated with $10^{-7}$ M 12(S)-HETE or ethanol (control) for the time indicated. Each point is an average (mean ± SE) from at least 3 separate experiments. Results are expressed as stimulation over control.

Example 8

Inhibition of 12(S)-HETE induced PAK activation by transient transaction by a PAK binding domain (PDB) plasmid.

The degree of 12(S)-HETE induce PAK activation was compared in CHO-$AT_{1a}$ cells which had been transiently transfected with a PDB plasmid and cells which had not been transfected.

Figure 8:
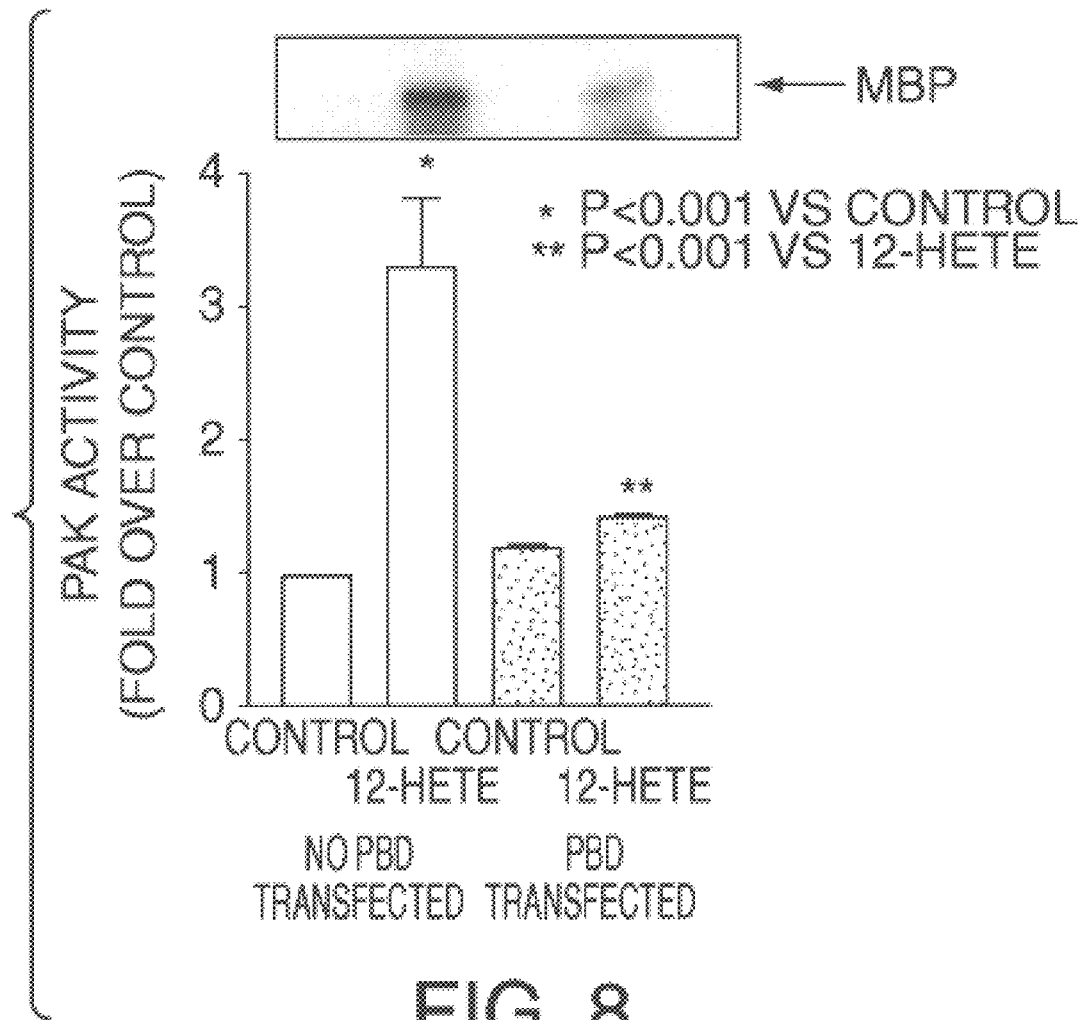
FIG. 8 shows the inhibitory effect of transient transfection of CHO-AT$_{1a}$ cells by a PBD plasmid on 12(S)-HETE-induced PAK activation.

For the PBD-transfected group, CHO-$AT_{1a}$ cells were transiently transfected with 15 µg PBD plasmid. For the non-PBD-transfected group, CHO-$AT_{1a}$ cells were treated with the same transfection reagents as the PBD-transfected group, but lacking plasmid. Plasmids used were endotoxin-free and prepared by EndoFree plasmid kit (Qiagen Co.) with the standard protocol. The DNA transfection method used was a cationic liposome-mediated transfection with DOSPER transfection reagent (Boehringer Manahein Co.) following the manufacturer's instructions. Briefly, the cells were plated the day before the transfection experiment at $3\times10^6$ cells per 100 mm dish. The next day, cells were washed with Opti-MEMd® reduced serum medium (Gibco BRL) and incubated in 5 ml of HAM's F-12 medium containing 1% FBS. Plasmid mixture (45 pµDUSPER/15 µg) was prepared and added to each dish. After a 5 hour incubation, the transfection medium was replaced and 8 ml fresh depletion medium (described in Example 7) continuing 1% FBS for overnight incubation was added. The cells were washed twice with depletion medium, incubated in the same medium for another 32 hours and harvested. Cells were then treated with $10^{-7}$M 12(S)-HETE or ethanol for 10 minutes. The top panel of FIG. 8 illustrates a representative autoradiogram of phosphorylated MBP bands from a gel. The bottom panel illustrates the densitometric quantification. Each point is an average (mean±SE) of at least 3 separate experiments. Results are expressed as stimulation over control. The PAK activity was measured as described in Example 7.

Example 9

Inhibition of PI 3-kinase by LY294002.

Figure 9:
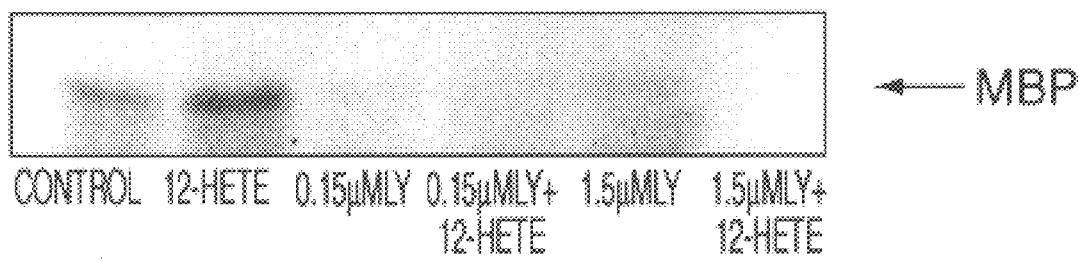
FIG. 9 is a representative autoradiogram of phosphorylated MBP bands demonstrating inhibition of 12(S)-HETE induced PAK activity by the PI 3-kinase inhibitor, LY294002.

Cells were pretreated with different concentrations of the PI-3 kinase inhibitor, LY294002 or DMSO (control) for 30 minutes, then treated with $10^{-7}$ M 12(S)-HETE or ethanol (control) for 10 minutes. PAK activity was measured as described in Example 7. FIG. 9 shows a representative autoradiogram of phosphorylated MBP bands from 3 similar experiments.

Example 10

Increased monocyte adhesion to HAEC by treatment of monocytes with 12(S)-HETE.

Monocytes were incubated with $10^{-9}$M 12(S)-HETE for 12 minutes at room temperature (RT) or 37° C. or left untreated at room temperature and assayed for monocytes adhesion. Eight fields were counted for each experiment. Results are presented in Table 1.

TABLE 1 effect of 12(S)-HETE on Monocyte Adhesion to Human Aortic Endothelial Cells

| Experiment | NT | 12(S)-HETE (RT) | 12(S)-HETE (37° C.) |
|---|---|---|---|
| 1 | 26.4 ± 12.5 | 39.6 ± 12.5[1] | 39.0 ± 9.3[3] |
| 2 | 28.3 ± 5.0 | 45.4 ± 7.6[2] | ND[4] |

[1]P = 0.016
[2]P = 0.001
[3]P = 0.01
[4]ND = not done

We claim:

1. A method for inhibiting the cellular effects of 12(S)-HETE on a cell having a 12(S)-HETE receptor, comprising administering to said cell a 12(S)-HETE receptor blocker.

2. The method of claim 1 wherein the 12(S)-HETE receptor is on the cell surface.

3. The method of claim 2 wherein the in the cells are selected from the group consisting of monocytes, endothelial cells, pancreatic islet beta cells, nerve cells, cardiac fibroblasts, cardiac myocytes and vascular smooth muscle cells.

4. The method of claim 1 wherein 12(S)-HETE binding is inhibited.

5. The method of claim 1 wherein receptor activation is inhibited.

6. The method of claim 1 wherein cell growth is inhibited.

7. The method of claim 1 wherein inflammatory cell damage is inhibited.

8. The method of claim 1 wherein cell death is inhibited.

9. The method of claim 1 wherein monocyte adhesion is reduced.

10. The method of claim 1 wherein VEGF production is reduced.

11. The method of claim 1 wherein PAK activation is reduced.

12. The method of claim 1 wherein the 12(S)-HETE receptor blocker is a 12(S)-HETE receptor antagonist.

13. The method of claim 1 wherein the 12(S)-HETE receptor blocker is an antibody.

14. A method of suppressing the activation of 12(S)-HETE receptors comprising the administration of a compound which prevents the binding of endogenous receptor agonists to the receptor.

15. The method of claim 1, wherein the 12(S)-HETE receptor blocker is selected from the group consisting of DuP654, Losartan, pertussis toxin, a 12(S)-HETE analog, an antibody to the 12(S)-HETE receptor, a peptide which binds to the 12(S)-HETE receptor and a peptide analog which binds to the 12(S)-HETE receptor.

* * * * *

UNITED STATES PATENT AND TRADEMARK OFFICE
CERTIFICATE OF CORRECTION

PATENT NO. : 6,046,224

DATED : April 4, 2000

Page 1 of 5

INVENTOR(S) : Rama Natarajan, et al.

It is certified that error appears in the above-identified patent and that said Letters Patent is hereby corrected as shown below: On title page: Item [56] insert the following:

U.S. PATENT DOCUMENTS

| DOCUMENT NUMBER | | | | | | | DATE | NAME | CLASS | SUBCLASS |
|---|---|---|---|---|---|---|---|---|---|---|
| 4 | 8 | 4 | 9 | 4 | 4 | 5 | 7/18/89 | Schaub | | |
| 5 | 2 | 4 | 6 | 9 | 7 | 0 | 9/21/93 | Williamson et al. | | |
| 5 | 6 | 8 | 6 | 4 | 9 | 6 | 11/11/97 | Anderskewitz et al | | |

NON-PATENT DOCUMENTS (Including Author, Title, Date, Pertinent Pages, Etc.)

Batt et al. "2-substituted-1-naphthols as potent 5-lipoxygenase inhibitors with topical antiinflammatory activity" J. Med. Chem. 33:360-370 (1990)

UNITED STATES PATENT AND TRADEMARK OFFICE
CERTIFICATE OF CORRECTION

PATENT NO. : 6,046,224

DATED : April 4, 2000

INVENTOR(S) : Rama Natarajan, et al.

It is certified that error appears in the above-identified patent and that said Letters Patent is hereby corrected as shown below:

Capodici et al., "Integrin-Dependent Homotypic Adhesion of Neutrophils" J. Clin. Invest. 102:165-175 (1998)

Chang et al. "Analysis of Integrin mRNA in Human and Rodent Tumor Cells" Biochem. Biophys. Res. Comm. 176:108-113 (1991)

Connolly, J.M., et al. "Effects of Eicosanoid Synthesis Inhibitors on Invasion f MDA-MB-435 Human Breast Cancer Cells in an In Vitro Assay System" Proc. Am. Assoc. Cancer Res. 35:52 abst. 312 (3/1994)

Corbett et al., "Aminoguanidine, a novel inhibitor of nitric oxide formation, prevents diabetic vascular dysfunction" Chem. Abstr. 116:248200t (1992)

Ellis et al., "Prevention of glomerular basement membrate thickening by aminoguanidine in experimental diabetes mellitus" Chem. Abstr. 115:150134d (1991)

Gross et al., "High-Affinity Binding and Lack of Growth-Promoting Activity of 12(S)-Hydroxyeicosatetraenoic Acid (12(S)-HETE) in a Human Epidermal Cell Line" J. Invest. Dermatol. 94:446-451 (1990)

Gu et al. "Ribozyme-mediated inhibition of expression of leukocyte-type 12-lipoxygenase in porcine aortic vascular smooth muscle cells" Circ. Res. 77:14-20 (1995)

Hammes et al., "Aminoguanidine treatment inhibits the development of experimental diabetic retinopathy" Chem. Abstr. 116:99146a (1992)

Herbertsson et al., "High-Affinity Binding Sites for 12(S)-hydroxy-5,8,10,14-eicosatetraenoic Acid (12(S)-HETE) in Carcinoma Cells" FEBS Lett. 298:249-252 (1992)

Herbertsson et al., "Subcellular Localization of 12(S)-hydroxy-5,8,10,14-eicosatetraenoic Acid Binding Sites in Lewis Lung Carcinoma Cells" Biochem. Biophys. Acta 1244:191-197 (1995)

Honn, K.V., et al. "A Lipoxygenase Metabolite, 12-(S)-HETE, Stimulates Protein Kiase C-Mediated Release of Cathepsin B from Malignant Cells" Exp. Cell Res. 214(1):120-130 (9/1994)

UNITED STATES PATENT AND TRADEMARK OFFICE
CERTIFICATE OF CORRECTION

PATENT NO. : 6,046,224

DATED : April 4, 2000

INVENTOR(S) : Rama Natarajan, et al.

It is certified that error appears in the above-identified patent and that said Letters Patent is hereby corrected as shown below:

---

Jost-Vu, E. et al., "Evidence for a Derangement in the Eicosanoid Pathway in Diabetes" Clin. Res. 40:106 (abstr.) (1992).

Kemeny, L., Ruzicka, T., "SC-41930, a leukotriene B4 receptor antagonist, inhibits 12(S)-hydroxyeicosatetraenoic acid (12(S)-HETE) binding to epidermal cells" Agents Actions 32(3-4):339-342 (March 1991)

Kemeny et al., "Dithranol-Induced Down-Regulation of 12(S)-hydroxyeicosatetraenoic Acid [12(S)-HETE] Receptors in a Human Epidermal Cell Line" Arch. Dermatol. Res. 283:333-336 (1991)

Kihara et al., "Aminoguanidine effects on nerve blood flow, vascular permeability, electrophysiology, and oxygen free radicals" Chem. Abstr. 115:85182b (1991)

Li, Maher, Schubert "A Role for 12-Lipoxygenase in Nerve Cell Death Caused by Glutathione Depletion" Neuron 19:453-463 (1997)

Liu et al., "12(S)-hydroxyeicosatetraenoic acid and 13(S)-hydroxyoctadecadienoic acid regulation of protein kinase C-$\alpha$ in melanoma cells: role of receptor-mediated hydrolysis of inositol phospholipids" Proc. Natl. Acad. Sci. USA 92:9323-9327 (1995)

Liu et al. "Lipoxygenase metabolites of arachidonic and linoleic acids modulate the adhesion of tumor cells to endothelium via regulation of protein kinase C" Cell Regulation 2:1045-1055 (12/1991)

Metz, S. et al.,"Glucose Increases the Syntehesis of Lipoxygenase-Mediated Metabolites of Arachidonic Acid in Intact Rat Islets" Proc. Natl. Acad. Sci. USA 82:198-202 (1985).

Natarajan et al., "Elevated Glucose and Angiotensin II Increase 12-Lipoxygenase Activity and Expression in Porcine Aortic Smooth Muscle Cells" Proc. Natl. Acad. Sci., USA 90:4947-4951 (1993)

Natarajan, et al., "Effects of High Glucose on Vascular Endothelial Growth Factor Expression in Vascular Smooth Muscle Cells" Am. J. Physiol. 273 (Heart Circ. Physiol. 42):H2224-H2231 (1997)

UNITED STATES PATENT AND TRADEMARK OFFICE
CERTIFICATE OF CORRECTION

PATENT NO. : 6,046,224
DATED : April 4, 2000
INVENTOR(S) : Rama Natarajan, et al.

It is certified that error appears in the above-identified patent and that said Letters Patent is hereby corrected as shown below:

Natarajan et al. "Role of the lipoxygenase pathway in angiotensin II-mediated aldosterone biosynthesis in human adrenal glomerulosa cells" HCAPLUS Abstract AN 1988:543217 (1988)

Natarajan, R., et al., "Role of Lipoxygenase Pathway in Angiotensin II-Induced Vascular Smooth Muscle Cell Hypertrophy" Hypertension 23 (Supp. I):I142-I147 (1994)

Natarajan, R., et al., "Role of the Lipoxygenase Pathway in Angiotensin II-Mediated Aldosterone Biosynthesis in Human Adrenal Glomerulosa Cells" J. Clin. Endocrinol. Metab. 67:584-591 (1988)

Natarajan et al., "Arachidonic Acid Metabolities on Renin and Vascular Smooth Muscle Cell Growth" Chapter 26 in: Contemporary Endocrinology: Endocrinology of the Vasculature (Sowers Ed.) Humana Press, Inc., Totowa, NJ, pp. 373-387, (6/96)

Nishio et al., "Role of the lipoxygenase pathway in phenylephrine-induced vascular smooth muscle cell proliferation and migration" European J. of Pharmacology 336:267-273 (1997)

UNITED STATES PATENT AND TRADEMARK OFFICE
CERTIFICATE OF CORRECTION

PATENT NO. : 6,046,224
DATED : April 4, 2000
INVENTOR(S) : Rama Natarajan et al

It is certified that error appears in the above-identified patent and that said Letters Patent is hereby corrected as shown below:

Nozawa et al., "Inhibition of Lipoxygenase Pathway Reduces Blood Pressure in Renovascular Hypertensive Rats" Am. J. Physiol. 259:H1774-H1780 (1990)

Stern, N., et al., "Selective inhibition of angiotensin II-mediated vasoconstriction by lipoxygenase blockade" Am. J. Physiol. 257:H434-H443 (1989)

Suss et al., "Regulation of 12(S)-Hydroxyeicosatetraenoic Acid (12(S)-HETE) Binding Sites on Human Epidermal Cells by Interferon-γ" Exptl. Cell Res. 191(2):204-208 (1990)

Vonakis, B.M., et al. "15-Hydroxyeicosatetraeonic Acid (15-HETE) Receptors" J. Biol. Chem. 267(33):23625-23631 (11/25/1992)

Signed and Sealed this

Eighteenth Day of July, 2000

Attest:

Q. TODD DICKINSON

*Attesting Officer*       *Director of Patents and Trademarks*